(12) United States Patent
Pisano et al.

(10) Patent No.: US 7,888,368 B2
(45) Date of Patent: Feb. 15, 2011

(54) TREATMENT OF DRUG-RESISTANT TUMORS

(75) Inventors: Claudio Pisano, Aprilia (IT); Loredana Vesci, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 12/096,884

(22) PCT Filed: Dec. 13, 2006

(86) PCT No.: PCT/EP2006/069666
§ 371 (c)(1),
(2), (4) Date: Jun. 26, 2008

(87) PCT Pub. No.: WO2007/071603
PCT Pub. Date: Jun. 28, 2007

(65) Prior Publication Data
US 2008/0312265 A1    Dec. 18, 2008

(30) Foreign Application Priority Data
Dec. 21, 2005   (EP) ................................. 05027997

(51) Int. Cl.
*A01N 43/42* (2006.01)
*A01N 43/00* (2006.01)
*A61K 31/44* (2006.01)
*A61K 31/33* (2006.01)
*C07D 471/00* (2006.01)
*C07D 491/00* (2006.01)
*C07D 498/00* (2006.01)
*C07D 513/00* (2006.01)
*C07D 515/00* (2006.01)

(52) U.S. Cl. ........................ 514/283; 514/280; 514/279; 514/183; 546/48

(58) Field of Classification Search ................. 514/283, 514/280, 279, 183; 546/48
See application file for complete search history.

(56) References Cited

FOREIGN PATENT DOCUMENTS

EP          1 044 977        10/2000
WO          WO 97/31003       8/1997

OTHER PUBLICATIONS

Dallavalle et al. Journal of Medicinal Chemistry, 2001, vol. 44, pp. 3264-3274.*
Serafin et al. The Journal of Urological Research, 2002, vol. 30, pp. 289-294.*
Tsurutani et al. Lung Cancer, Mar. 2002, vol. 35, Issue 3, pp. 299-304, Abstract.*

* cited by examiner

*Primary Examiner*—Sreeni Padmanabhan
*Assistant Examiner*—Samira Jean-Louis
(74) *Attorney, Agent, or Firm*—Lucas & Mercanti, LLP

(57) ABSTRACT

A subclass of camptothecin derivatives is disclosed to be useful for the preparation of a medicament for the treatment of drug-resistant tumors and/or for the administration to patients who show polymorphisms in the gene coding for DNA topoisomerase I.

2 Claims, 1 Drawing Sheet

TREATMENT OF DRUG-RESISTANT TUMORS

FIELD OF THE INVENTION

The present invention relates to the use of a subclass of camptothecin derivatives for the preparation of a medicament for the treatment of drug-resistant tumors and/or for the administration to patients who show polymorphisms in the gene coding for DNA topoisomerase I.

BACKGROUND OF THE INVENTION

Camptothecin derivatives are DNA-topoisomerase I inhibitors that have emerged as a prominent class of anticancer agents. Together with the taxanes, the topoisomerase I inhibitors are presumably the most important new class of anticancer drugs introduced into clinical practice. Pre-clinical studies demonstrated significant in vitro and in vivo activity of topoisomerase I inhibitors, such as camptothecin and its derivatives, on a broad range of tumors. The results from clinical trials were promising, as shown by the registration of two topoisomerase inhibitors, topotecan and irinotecan (also known as CPT-11), in many European countries and in the USA, for treatment of patients with ovarian and colorectal cancer, respectively. Other derivatives are currently at different stages of clinical development.

In patent application EP1044977 and in J. Med. Chem. 2001, 44, 3264-3274, camptothecin derivatives are described which bear an alkyloxime O-substituted at position 7 and which are endowed with antitumor activity higher than the compound of reference topotecan. Moreover these camptothecin derivatives bearing an imino group on position 7, also show an improved therapeutic index. Among these compounds one of the preferred molecules was shown to be 7-t-butoxyiminomethylcamptothecin (CPT 184, also known as ST1481 or gimatecan).

The main property of camptothecin analogues is their activity against DNA topoisomerase I, but beyond this similarity the compounds differ widely in terms of antitumor activity, pharmacology and metabolism. Despite the good tolerability and efficacy of camptothecins in animal models, their low therapeutic index still remains a major drawback for their clinical use, together with the reversibility of the drug interaction in the ternary complex (drug-enzyme-DNA) and the instability of the lactone ring, which preclude their efficacy against slowly-growing tumors. Lastly, experimental models showed that camptothecins anti-tumor activity is strongly dependent upon the drug administration schedule, in fact require either a prolonged schedule of administration at low doses, or frequent intermittent dosing schedules.

Although new cancer drugs have been developed and consequently some malignancies are now curable, drug resistance to chemotherapies, including camptothecin derivatives, is a major limitation to therapy in several human tumours and there are still numerous primary and recurrent, refractory cases. DNA topoisomerase I has recently been investigated to define the mechanism in naïve or acquired resistance to Topotecan or CPT-11 and several mutations that impact on resistance to camptothecin derivatives have been identified in several regions of human topoisomerase I (Benedetti et al. 1993. Cancer Res 53. 4343; Fiorani et al. J Biol. Chem. 2003; Oct. 31; 278 (44):43268-75; Chrencik et al. 2004; JMB 339, 773-784).

Furthermore mutations in topoisomerase I occurred after chemotherapy with CPT-11 in NSCLC patients suggested that the development of resistance to irinotecan in some patients may involve topoisomerase I mutation (Tsurutani et al. 2002 Lung cancer 35. 299-304).

Although the significance of topoisomerase I mutations to CPT resistance needs to be further investigated, it is considered of great clinical interest to have a camptothecin derivative that, besides its typical pharmacological profile, shows an activity on mutated topoisomerase I.

DESCRIPTION OF THE INVENTION

Using wild-type and two mutated human topoisomerases I, that confers resistance to the camptothecin derivatives (i.e. camptothecin, topotecan, SN-38), we surprisingly discovered that some camptothecin derivatives (see the results for ST1968 and ST1969) are able to inhibit wild-type Topoisomerase I as well as mutated human topoisomerases I.

Therefore the main object of the present invention is the use of a compound for Formula I,

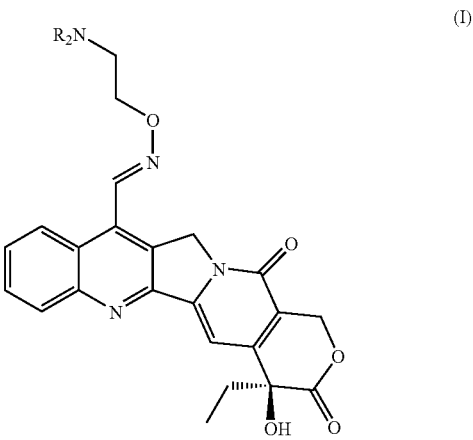

where R is hydrogen or $C_1$-$C_4$ alkyl for the preparation of a medicament for the treatment of drug-resistant tumors and/or for the administration to patients who show polymorphisms in the gene coding for DNA topoisomerase I.

Such polymorphisms in the gene coding for DNA topoisomerase I can be native or can develop in some patients further to pharmaceutical treatment, for example further to treatment with camptothecins.

Compounds of Formula (I) also comprise tautomers, geometrical isomers, optically active forms as enantiomers, diastereomers and racemate forms, as well as pharmaceutically acceptable salts of the compounds of Formula (I).

Preferred pharmaceutically acceptable salts of the Formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

Preferably R is hydrogen or methyl.

Preferred compounds of Formula (I) are:

7-(2-amino)ethoxyiminomethylcamptothecin, (ST1968, also known as CPT188) and 7-(2-dimethylamino)ethoxyiminomethylcamptothecin (ST1969).

The drug-resistant tumor pathology that can be treated according to the present invention is selected from the group consisting of sarcoma, ovarian carcinoma, particularly prostate carcinoma, carcinoid bone tumour, neuroendocrine tumour, lymphoid leukaemia, acute promyelocytic leukaemia, myeloid leukaemia, monocytic leukaemia, megakaryoblastic leukaemia and Hodgkin's disease.

The compounds of Formula (I) may be prepared from readily available starting materials using the following general methods and procedures. It will be appreciated that where typical or preferred experimental conditions (i.e. reaction temperatures, time, moles of reagents, solvents, etc.) are given, other experimental conditions can also be used, unless otherwise stated. Optimum reaction conditions may vary with the particular reactants or solvents used, but such conditions can be determined by one skilled in the art by routine optimisation procedures. Specific reference is made to the methods described in patent application EP1044977 and in J. Med. Chem. 2001, 44, 3264-3274.

A method of treating a mammal suffering from a drug-resistant tumour pathology, comprising administering a therapeutically effective amount of a compound of Formula (I) as described above represents one of the aspects of the present invention.

Therefore, according to the present invention, a patient suffering from a tumor pathology, which has proven to be resistant to the treatment of commonly prescribed antitumor drugs, such as, camptothecins (e.g. irinotecan, topotecan, gimatecan), platinum complexes (e.g. carboplatin) or taxanes (e.g. paclitaxel, docetaxel), may be successfully treated with a compound of Formula (I)

The term "therapeutically effective amount" as used herein refers to an amount of a therapeutic agent needed to treat, ameliorate a targeted disease or condition, or to exhibit a detectable therapeutic effect.

For any compound, the therapeutically effective dose can be estimated initially either in cell culture assays, for example, of neoplastic cells, or in animal models, usually mice or rats.

The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination (s), reaction sensitivities, and tolerance/response to therapy. This amount can be determined by routine experimentation and is within the judgement of the clinician. Generally, an effective dose will be from 0.01 mg/kg to 100 mg/kg, preferably 0.05 mg/kg to 50 mg/kg. Compositions may be administered individually to a patient or may be administered in combination with other agents, drugs or hormones.

The medicament may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal, rectal means or locally on the diseased tissue after surgical operation.

Dosage treatment may be a single dose schedule or a multiple dose schedule.

The invention will now be illustrated in greater detail by means of non-limiting Examples and Figures.

EXAMPLES

Example 1

Figure 1:
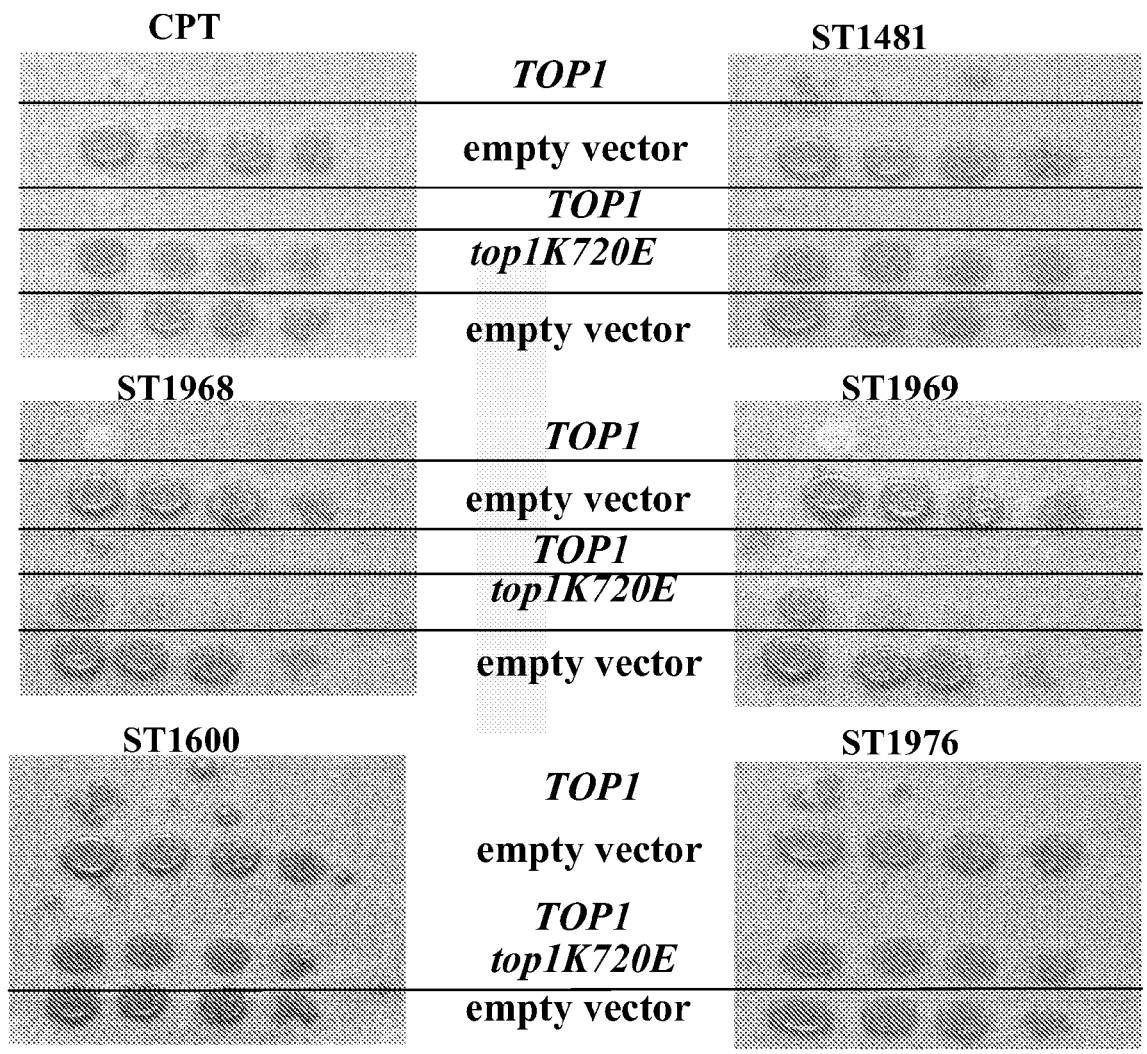
FIG. 1 shows the in vivo effect of some camptothecin derivatives on human DNA topoisomerase I wild type or mutant expressed in the *Saccharomyces cerevisiae* yeast. Cultures of yeast cells transformed with YcpGal1hTOP1 (WT), YcpGal1htop1K720E and YcpGal1 (empty vector) were serially diluted (10-fold dilution from left to right) and spotted onto uracil-minus minimal agar plates containing 2% galactose and 45 µM of camptothecin, ST1481, ST1968, ST1969, ST1600 and ST1976.

In Vivo Effect of Some Camptothecin Derivatives on Human DNA Topoisomerase I Wild Type or Mutant Expressed in *Saccharomyces cerevisiae*

Methods

*Saccharomyces cerevisiae* strain used to clone wild-type human topoisomerase I (hTOP1) and the mutated topoisomerase I was: EKY2 (MATα, ura3-52, his3Δ200, leu 2Δ1, trp1Δα63, top1::TPR1) as described by Bjornsti et al 1989 (Cancer Res. 49, 6318-6323). The plasmids used to transform yeast carrying the wild type full-length human Topoisomerase I (YCpGAL1hTOP1) was described by Bjornsti et al 1989 (Cancer Res. 49, 6318-6323) and the mutated Topoisomerase I YCpGAL1htop1K720E was generated by oligonucleotide-directed mutagenesis using a method described by Fiorani et al. 1998 (J. Biol. Chem. 14, 8425-8433): In both plasmids Topoisomerase expression were under the control of a galactose-inducible promoter of the yeast GAL1.

Before to transform the yeast cells with DNA (lithium acetate method), yeast was grown on solid medium. It was streaked on plates of 90 mm containing sterile solid medium (YPDA) (10 g yeast, 20 g peptone, 20 g dextrose, 0.7 g adenine, 20 g glucose, 20 g agar for liter). Colonies were grown after 48 h at 30° C. One day before the transformation, a single yeast colony of the strain to be transformed was inoculated in 5 ml of steril liquid YPDA (the medium above mentioned without agar). The colony was grown to saturation overnight under stirring at 30° C. The day after, 5 ml of saturated culture was diluted in 100 ml of YPDA liquid medium and grown at 30° C. to reach an optical density of 1.0 at 600 nm. Cells were centrifuged for 5 min at 4000×g at room temperature and the pellet was resuspended in 25 ml of a solution (T/E) containing 10 mM Tris-EDTA pH7.5, 1 mM EDTA and 100 mM lithium acetate. The yeast suspension was centrifuged for 5 min at 4000×g at room temperature. The pellet was resuspended in a fresh solution above described (about 500 µl) to obtain 2×10$^9$ cells/ml. To have the transformation, 200 µg of DNA carrier were mixed with 1 µg transforming DNA and 200 µl yeast cells in an eppendorf. Subsequently, 1.2 ml of a solution TE/lithium acetate containing 40% PEG were added and the yeast suspension was kept under stirring for 30 min at 30° C. A heat shock was performed by keeping the yeast suspension at 42° C. for 15 min. Subsequently it was centrifuged 5 sec at room temperature. Yeast was resuspended in TE buffer and spread up onto CM (complete minimal) dropout medium on plates. CM was previously prepared with 1.3 g of dropout powder containing different aminoacids without uracil, 1.7 g yeast nitrogen base without aminoacids and ammonium sulfate, 5 g ammonium sulfate, 20 g glucose and 20 of agar for liter). The plates were incubated at 30° C. until transformants appear.

To perform the in vivo spot test, the transformants were inoculated in 5 ml of steril liquid CM medium and grown overnight under stirring at 30° C. The day after a dilution of the yeast colonies was made to reach an optical density at 600 nm of 0.3. Starting from this first dilution, other serial dilutions (1:10, 1:100, 1:1000) were performed in plates of 96 well. 5 µl of each dilution were put on plates of 90 mm containing solid CM medium. For the control samples, 2% glucose or 2% galactose were added; for the camptothecin-derivatives treated samples, 2% galactose and the drugs at a concentration 45 µM were added. The yeast colonies were incubated at 30° C. for 48-72 h and analyzed macroscopically.

Results

The activity of camptothecin derivatives was evaluated on the viability of yeast cells transformed with human DNA topoisomerase I wild type (YCpGAL1 hTOP1) or human DNA topoisomerase I mutant YCpGAL1htop1K720E in terms of number of yeast growing colonies in agar. ST1968, ST1969, ST1481 (gimatecan), ST1600 (7-[2-(4-morpholinyl)ethoxy]iminomethylcamptothecin) and ST1976 (7-(4-amino)benzyloxyiminomethylcamptothecin) and the camptothecin (CPT) showed to inhibit the growth of the yeasts transformed with the DNA topoisomerase I wild type (FIG. 1). Surprisingly, only ST1968 and ST1969 were able to inhibit the growth of the transformed YCpGAL1htop1K720E mutant (see FIG. 1).

Cultures of yeast cells transformed with YcpGal1hTOP1 (WT), YcpGal1htop1K720E and YcpGal1 (empty vector) were serially diluted (10-fold dilution from left to right) and spotted onto uracil-minus minimal agar plates containing 2% galactose and 45 µM of camptothecin, ST1481, ST1968, ST1969, ST1600 and ST1976.

Example 2

In Vivo Antitumoral Activity on Drug-Resistant Tumor Xenograft Models

ST1968 showed a wide spectrum of efficacy against different resistant xenograft tumor models. Using a q4d dosing schedule repeated for 3-5 doses, ST1968 was compared to irinotecan or other known chemotherapeutic agents against different human tumor models (Table 2), including A2780/ADR multidrug-resistant ovarian carcinoma which overexpresses PgP glycoprotein, A2780/DDP platinum-resistant ovarian carcinoma and DU145RC1 camptothecin-resistant prostate carcinoma which was previously selected by continuous exposure of the parental sensitive DU145 to 9-nitro-camptothecin (Urasaki Y et al., 2001, *Cancer Res* 61, 1964-9). On this selected tumor cell line, a Topoisomerase I mutation which changes the arginine 364 codon to histidine (R364H) was found. The 364H point mutation was located in the highly conserved core, a region of Topoisomerase I within the Topoisomerase I amino acid residues 361-364 critical for camptothecin resistance. Moreover, this mutation site is close to the catalytic tyrosine. The resistance of the Topoisomerase I/R364H is probably attributable to the loss of a critical H-bond between R364 and camptothecin E-ring lactone moiety.

Methods

Exponentially growing tumor cells were injected s.c. into nude athymic mice. The number of tumor cells was previously chosen by a growth curve. Mice were housed inside cages of makrolon (33.2×15×13 cm) with stainless steel cover-feed and sterilized and dust-free bedding cobs. Animals were housed under a light-dark cycle, keeping temperature and humidity constant. Parameters of the animal rooms were assessed as follows: 22±2° C. temperature, 55±10% relative humidity, about 15-20 filtered air changes/hour and 12 hour circadian cycle of artificial light (7 a.m., 7 p.m.). At request, the environmental conditions were monitored and the data are retained in Animal Housing Archives. Drinking water was supplied ad libitum. Each mouse was offered daily a complete pellet diet (GLP 4RF21, Mucedola) throughout the study. The analytical certificates of animal food and water are retained at Sigma-Tau premises. All animals were weighed before starting the experiment and were subdivided into the different dosage groups. Each cage was identified by a paper tag indicating: cage number, group, date of tumor injection, starting date of treatment, name of the test item, dose and route of administration, date of sacrifice.

Tumor growth was followed by biweekly measurements of tumor diameters with a Vernier caliper. Tumor volume (TV, mm$^3$) was calculated as: [length (mm)×width (mm)$^2$]/2, where the width and the length are the shortest and the longest diameters of each tumor, respectively.

The efficacy of the drug treatment was assessed as: a) Tumor volume inhibition (TVI %) in treated versus control mice, calculated as: 100−[(mean tumor volume of treated animals/mean tumor volume of control animals)×100]; b) LCK ($\log_{10}$ cell kill) calculated by the formula LCK=(T−C)/3.32×DT, where T and C are the mean times (days) required for treated (T) and control (C) tumor, respectively, to reach 1000 mm$^3$, and DT is the doubling time of control tumors; CR meaning no evidence of tumor lasting for at least 10 days.

The toxicity of the drug treatments was determined as: body weight loss percent (% BWL max)=100−(mean $BW_{day\,x}$/mean $BW_{day\,1}$×100), where $BW_x$ is the mean BW at the day of maximal loss during the treatment and $BW_1$ is the mean BW on the 1$^{st}$ day of treatment.

Results

The efficacy of ST1968 in terms of tumor volume inhibition (TVI %) or log cell kill (LCK) or complete response (CR) against three different resistant tumor xenograft models was substantially improved compared with irinotecan or topotecan or chemotherapeutic agents such as paclitaxel and carboplatin (see Table 2). In particular, ST1968 showed a higher antitumor effect in terms of number of complete responses at least 10 days after the last treatment. Moreover ST1968 revealed a high persistence of action on tumor growth after the end of the treatment, since LCK was higher than that found with the other drugs.

Surprisingly, the efficacy of ST1968 in terms of tumor volume inhibition (TVI %) or log cell kill (LCK) against mutated Topisomerase I DU145RC.1 was increased respect to that observed against DU145 sensitive prostate carcinoma.

TABLE 2

Antitumor activity of ST1968 on human resistant tumor xenograft models

| Tumor | Line | Compound | Dose (mg/kg) | Method of administ. | TVI % | LCK | CR |
|---|---|---|---|---|---|---|---|
| Ovarian ca. | A2780/ADR | ST1968 | 30 | q4d × 4 | 100 | 1.9 | 8|8 |
| | | ST1968 | 15 | q4d × 4 | 99 | 2.2 | 6/8 |
| | | topotecan | 10 | q4d × 4 | 85 | 1.1 | 1/6 |
| | | paclitaxel | 16 | q4d × 4 | 16 | 0.1 | 0/8 |
| | | carboplatin | 33.3 | q4d × 4 | 62 | 0.6 | 0/7 |
| | A2780/DDP | ST1968 | 30 | q4d × 3 | 100 | >>6.3 | 7/7 |
| | | ST1968 | 15 | q4d × 3 | 100 | 6.3 | 8/8 |
| | | topotecan | 10 | q4d × 3 | 93 | 1.2 | 1/8 |
| | | paclitaxel | 15 | q4d × 3 | 94 | 1.4 | 6/6 |
| | | carboplatin | 25 | q4d × 3 | 26 | 0.5 | 0/8 |
| Prostate ca. | DU145 RC1 | ST1968 | 30 | q4d × 5 | 65 | 1.3 | 0/8 |
| | | irinotecan | 60 | q4d × 5 | 45 | 0.8 | 0/8 |
| | DU145 | ST1968 | 35 iv | q4d × 4 | 66 | 0.65 | |

The invention claimed is:

1. Method of treating a mammal suffering from a drug-resistant prostate carcinoma comprising administering a therapeutically effective amount of a compound of Formula I,

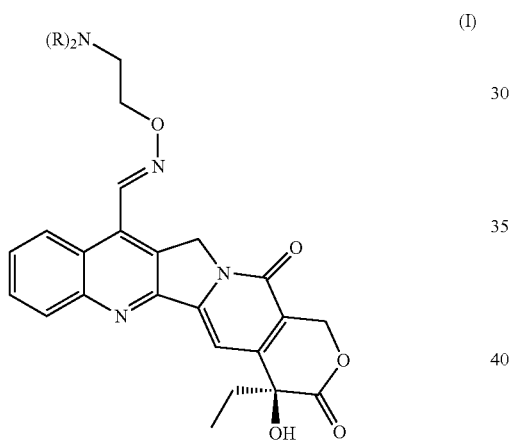

(I)

where $(R)_2$ is hydrogen or $C_1$-$C_4$ alkyl, to said mammal in need thereof, wherein said mammal shows polymorphism in the gene coding for DNA topoisomerase I.

2. The method according to claim 1 wherein $(R)_2$ is hydrogen or methyl.

* * * * *